US008945620B2

(12) United States Patent
Bockbrader et al.

(10) Patent No.: US 8,945,620 B2
(45) Date of Patent: Feb. 3, 2015

(54) SOLID PHARMACEUTICAL COMPOSITIONS CONTAINING PREGABALIN

(71) Applicant: Warner-Lambert Company LLC, New York, NY (US)

(72) Inventors: Howard N. Bockbrader, Ann Arbor, MI (US); Yun Hyung Cho, Lexington, MA (US); Steven Diaz Santiago, Martinsville, NJ (US); Majid Mahjour, Schwenksville, PA (US); Thomas Daniel Reynolds, Morgantown, WV (US); Pushpa Ganapathi Shao, San Diego, CA (US); Zezhi Jesse Shao, San Diego, CA (US); Jiansheng Wan, Short Hills, NJ (US)

(73) Assignee: Warner-Lambert Company LLC, New York, NY (US)

( * ) Notice: Subject to any disclaimer, the term of this patent is extended or adjusted under 35 U.S.C. 154(b) by 0 days.

(21) Appl. No.: 14/181,785

(22) Filed: Feb. 17, 2014

(65) Prior Publication Data

US 2014/0163103 A1  Jun. 12, 2014

Related U.S. Application Data

(63) Continuation of application No. 13/947,433, filed on Jul. 22, 2013, now abandoned, which is a continuation of application No. 13/706,971, filed on Dec. 6, 2012, now abandoned, which is a continuation of application No. 13/472,704, filed on May 16, 2012, now abandoned, which is a continuation of application No. 13/267,352, filed on Oct. 6, 2011, now abandoned, which is a continuation of application No. 11/555,988, filed on Nov. 2, 2006, now abandoned.

(60) Provisional application No. 60/732,589, filed on Nov. 2, 2005.

(51) Int. Cl.
| | |
|---|---|
| A61K 9/22 | (2006.01) |
| A61K 47/32 | (2006.01) |
| A61K 9/00 | (2006.01) |
| A61K 31/197 | (2006.01) |
| A61K 47/34 | (2006.01) |
| A61K 9/20 | (2006.01) |

(52) U.S. Cl.
CPC ............... *A61K 47/32* (2013.01); *A61K 9/0065* (2013.01); *A61K 31/197* (2013.01); *A61K 47/34* (2013.01); *A61K 9/2027* (2013.01)
USPC .......................................................... 424/468

(58) Field of Classification Search
None
See application file for complete search history.

(56) References Cited

U.S. PATENT DOCUMENTS

| | | | |
|---|---|---|---|
| 5,563,175 | A | 10/1996 | Silverman et al. |
| 5,599,973 | A | 2/1997 | Silverman et al. |
| 5,608,090 | A | 3/1997 | Silverman et al. |
| 5,616,793 | A | 4/1997 | Huckabee et al. |
| 5,629,447 | A | 5/1997 | Huckabee et al. |
| 5,637,767 | A | 6/1997 | Grote et al. |
| 5,684,189 | A | 11/1997 | Silverman et al. |
| 5,710,304 | A | 1/1998 | Silverman et al. |
| 5,840,956 | A | 11/1998 | Grote et al. |
| 5,847,151 | A | 12/1998 | Silverman et al. |
| 6,028,214 | A | 2/2000 | Silverman et al. |
| 6,046,353 | A | 4/2000 | Grote et al. |
| 6,054,482 | A | 4/2000 | Augart et al. |
| 6,261,601 | B1 | 7/2001 | Talwar et al. |
| 6,359,169 | B1 | 3/2002 | Silverman et al. |
| 6,635,279 | B2 | 10/2003 | Kolter et al. |
| 2003/0100611 | A1 | 5/2003 | Berner et al. |
| 2003/0212290 | A1 | 11/2003 | Burk et al. |

FOREIGN PATENT DOCUMENTS

| | | | |
|---|---|---|---|
| EP | 1294363 | B1 | 12/2003 |
| WO | 9959572 | | 11/1999 |
| WO | 9959573 | | 11/1999 |
| WO | 0197612 | A1 | 12/2001 |
| WO | 0226263 | A2 | 4/2002 |

OTHER PUBLICATIONS

Almarsson et al., "Crystal engineering of the composition of pharmaceutical phases. Do pharmaceutical co-crystals represent a new path to improved medicines?", Chem. Comm., (2004) 1889-1896.
Berge, et al. "Pharmaceutical Salts", J. Pharm. Sci., (1977) 1-19, vol. 66(1).
Haleblian, "Characterization of Habits and Crystalline Modification of Solids and Their Pharmaceutical Applications", J. Pharm. Sci., (1975), 1269-88, vol. 64(8).
Buhler, Volker. Polyvinylpyrrolidone—Excipients for Pharmaceuticals: Povidone, Crospovidone and Copovidone, 2005, Springer-Verlag, Berlin, Germany.
Kolter, K. Properties of Kollidon(R), SR as a New Excipient for Sustained Release Dosage Forms. Abstract. American Association of Pharmaceutical Scientists 1999 meeting.

(Continued)

*Primary Examiner* — Paul Dickinson
(74) *Attorney, Agent, or Firm* — J. Michael Dixon

(57) ABSTRACT

A solid pharmaceutical composition containing pregabalin is described. The composition includes a matrix forming agent and a swelling agent and is suitable for once daily oral administration. Exemplary matrix forming agents include mixtures of polyvinyl acetate and polyvinylpyrrolidone, and exemplary swelling agents include cross-linked polymers of polyvinylpyrrolidone.

17 Claims, No Drawings

(56) References Cited

OTHER PUBLICATIONS

Ruchatz, F. Kollidon(R) SR—a New Excipient for Sustained Release Matrices, Proceed. Int'l. Symp. Control. Rel. Bioact. Mater., Controlled Release Society, Inc.. Revised Jul. 1999, pp. 869-870, 26.
English Translation of the fillings to date for the Opposition filed against Israeli Patent Application No. 190827 by Teva, 2014.
Submission under Article 100 (a) EPC, by an unnamed 3rd party seeking the revocation of European Patent 1945186B, 2014.
Committee for Propriety Medicinal Products (CPMP), Note for Guidance on Modified Release Oral and Transdermal Dosage Forms: Section II (Pharmacokinetic and Clinical Evaluation). The European Agency for the Evaluation of Medicinal Products, Human Medicines Evaluation Unit, Jul. 28, 1999, pp. 1-11, London.
Guidance for Industry, Bioavailability and Bioequivalence Studies for Orally Administered Drug Products—General Considerations, U.S. Department of Health and Human Services, Food and Drug Administration, Center for Drug Evaluation and Research (CDER), Mar. 2003, Rev. 1, pp. 1-23.
Draganoiu, et al. Evaluation of the New Polyvinylacetate/Povidone Excipient for Matrix Sustained Release Dosage Forms. Pharm Ind, 201, 63(6), 624-629, 2014.
Chawla, et al., Gastroretention, A Means to Address Regional Variability in Intestinal Drug Absorption, Pharmaceutical Technology, Jul. 2003, 50-65, 2014.
Frampton, et al., Pregabalin In the Treatment of Painful Diabetic Peripheral Neuropathy, Drugs, 2004, 64(24), 2813-2820.
Hou, et al., Gastric Retentive Dosage Forms: A Review, Clin Rev in Therapeutic Drug Carrier Systems, 2003, 20(6), 461-497.
Deshpande, et al., Development of a Novel Controlled-Release System for Gastric Retention, Pharm Res, 1997, 14 (6), 815-819.
Fussnegger, Kollidon Sr: A polyvinyl acetate based excipient for DC-sustained-release oral dosage forms, Internet Publication from Jun. 2003.

SOLID PHARMACEUTICAL COMPOSITIONS CONTAINING PREGABALIN

CROSS REFERENCE

This application is a continuation of U.S. patent application Ser. No. 13/947,433, filed Jul. 22, 2013, which is a continuation of U.S. patent application Ser. No. 13/706,971, filed Dec. 6, 2012, which is a continuation of U.S. patent application Ser. No. 13/472,704, filed May 16, 2012, which is a continuation of U.S. patent application Ser. No. 13/267,352, filed Oct. 6, 2011, which is a continuation of U.S. patent application Ser. No. 11/555,988, filed Nov. 2, 2006, which claims the benefit of U.S. Patent Application Ser. No. 60/732,589, filed Nov. 2, 2005, the contents of each which are incorporated by reference.

BACKGROUND OF THE INVENTION

This invention relates to solid pharmaceutical compositions containing pregabalin which are suitable for once daily (QD) oral dosing.

Pregabalin, or (S)-(+)-3-aminomethyl-5-methyl-hexanoic acid, binds to the alpha-2-delta ($\alpha 2\delta$) subunit of a calcium channel and is related to the endogenous inhibitory neurotransmitter $\gamma$-aminobutyric acid (GABA), which is involved in the regulation of brain neuronal activity. Pregabalin exhibits anti-seizure activity, as discussed in U.S. Pat. No. 5,563,175 to R. B. Silverman et al., and is useful for treating, among other conditions, epilepsy, pain, physiological conditions associated with psychomotor stimulants, inflammation, gastrointestinal damage, alcoholism, insomnia, fibromyalgia, and various psychiatric disorders, including anxiety, depression, mania, and bipolar disorder. In the United States, pregabalin has been approved for the treatment of diabetic peripheral neuropathy, postherpetic neuralgia, and as an adjunctive treatment for partial onset seizures in adults. Pregabalin is available as an immediate release (IR) formulation in capsules and is administered to patients two- or three-times daily (BID or TID).

Many patients receiving pregabalin or other drugs which are administered two or more times daily would likely benefit from once daily dosing. The convenience of QD dosing generally improves patient compliance, especially for elderly patients and for patients taking multiple medications. Once per day dosing may also lessen or prevent potentially undesirable dose-related effects by reducing peak blood levels ($C_{MAX}$) and may also increase drug efficacy by increasing minimum plasma concentrations ($C_{MIN}$).

Once daily dosing of pregabalin, however, presents numerous challenges. Conventional extended release (ER) compositions are problematic for QD dosing because pregabalin is not absorbed uniformly in the gastrointestinal (GI) tract. Clinical studies indicate that pregabalin is absorbed in the small intestine and the ascending colon in humans, but is poorly absorbed beyond the hepatic flexure. This suggests that the mean absorption window for pregabalin is, on average, about six hours or less—any drug release from a conventional ER dosage form beyond six hours would thus be wasted because the dosage form has traveled beyond the hepatic flexure. Furthermore, pregabalin is a $\gamma$-amino acid which under normal storage conditions may undergo intramolecular cyclization to form a lactam, 4-isobutyl-pyrrolidin-2-one. See, e.g., WO 99/10186 and WO 99/59573, both to A. Aomatsu. Although it is known that the non-active components of the pharmaceutical composition may affect lactam formation, it is difficult to predict which excipients may lead to undesirable lactam formation.

SUMMARY OF THE INVENTION

The present invention provides a stable pharmaceutical composition containing pregabalin that is useful for once daily oral dosing. When administered as a solid dosage form, such as a tablet, the pharmaceutical composition is retained in the stomach for a longer period of time than an IR dosage form. While it is retained in the stomach, the pharmaceutical composition continuously releases pregabalin. Eventually, the pharmaceutical composition passes out of the stomach and into the small intestine where it may continue to release pregabalin. Extending the period of time during which pregabalin is released in the stomach effectively widens the absorption window associated with IR dosing, thereby permitting QD dosing. Furthermore, stability studies suggest that none of the components of the pharmaceutical composition promote undesirable lactam formation.

One aspect of the invention provides a pharmaceutical composition which is suitable for QD dosing and includes an active pharmaceutical ingredient and excipients. The active pharmaceutical ingredient includes pregabalin, or a pharmaceutically acceptable complex, salt, solvate or hydrate of pregabalin, and the excipients include a matrix forming agent and a swelling agent. The matrix forming agent includes polyvinyl acetate (PVAc) and polyvinylpyrrolidone (PVP), and the swelling agent includes cross-linked polyvinylpyrrolidone. The active pharmaceutical ingredient typically comprises from about 5% to about 60% of the pharmaceutical composition by weight; the matrix forming agent typically comprises from about 5% to about 45% of the pharmaceutical composition by weight, and the swelling agent typically comprises from about 5% to about 70% of the pharmaceutical composition by weight.

A further aspect of the invention provides a solid dosage form, such as a tablet, which is adapted for once daily oral dosing. The solid dosage form comprises the pharmaceutical composition described above. Upon contact with water, which is present, for example, in the gastric fluid of humans, the dosage form swells or expands to a size of about 9 mm or greater.

An additional aspect of the invention provides a method of treating a condition or disorder in a subject that is responsive to pregabalin. The method includes orally administering to the subject once per day the pharmaceutical composition described above.

Another aspect of the invention provides a method of treating a condition or disorder in a subject that is responsive to pregabalin, the method comprising orally administering to the subject a pharmaceutical composition once daily. The pharmaceutical composition comprises pregabalin and one or more excipients. The composition is adapted to provide the subject in any 24-hour period with a single steady-state maximum pregabalin concentration of 9 µg/mL or less and a steady-state minimum pregabalin concentration of about 0.7 µg/mL or greater.

DETAILED DESCRIPTION

Definitions and Abbreviations

Unless otherwise indicated, this disclosure uses the following definitions.

"About," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

"Subject" refers to a mammal, including a human.

"Pharmaceutically acceptable" substances refers to those substances which are within the scope of sound medical judgment suitable for use in contact with the tissues of subjects without undue toxicity, irritation, allergic response, and the like, commensurate with a reasonable benefit-to-risk ratio, and effective for their intended use.

"Treating" generally refers to reversing, alleviating, inhibiting the progress of, or preventing a disorder or condition in a subject, or to preventing one or more symptoms of such disorder or condition in the subject.

"Treatment" refers to the act of "treating" as defined immediately above.

"Drug," "drug substance," "active pharmaceutical ingredient," and the like, refer to a compound (e.g., pregabalin) that may be used for treating a subject in need of treatment.

"Therapeutically effective amount" of a drug refers to the quantity of the drug that may be used for treating a subject and is generally in the range of about 0.001 to about 100 mg/kg/day for an adult, and is often in the range of about 0.1 to about 50 mg/kg/day for an adult. For an adult human, a typical daily dose of a drug is in the range of about 1 mg to about 1000 mg. For pregabalin, the daily dose for an adult human may be in the range of about 50 mg to about 1800 mg and is often in the range of about 50 mg to about 900 mg.

"Inert" substances refer to those substances that may influence the bioavailability of the drug, but are otherwise pharmaceutically inactive.

"Excipient" or "adjuvant" refers to any inert substance.

"Pharmaceutical composition" refers to the combination of one or more drug substances and one or more excipients.

"Drug product," "pharmaceutical dosage form," "dosage form," "final dosage form" and the like, refer to a pharmaceutical composition that is administered to a subject in need of treatment and generally may be in the form of tablets, capsules, sachets containing powder or granules, liquid solutions or suspensions, patches, and the like.

"Solvate" describes a molecular complex comprising the drug substance (e.g., pregabalin) and a stoichiometric or non-stoichiometric amount of one or more pharmaceutically acceptable solvent molecules (e.g., ethanol). When the solvent is tightly bound to the drug the resulting complex will have a well-defined stoichiometry that is independent of humidity. However, when the solvent is weakly bound, as in channel solvates and hygroscopic compounds, the solvent content will be dependent on humidity and drying conditions. In such cases, the complex will often be non-stoichiometric.

"Hydrate" describes a solvate comprising the drug substance and a stoichiometric or non-stoichiometric amount of water.

"Retained in the stomach," when used in connection with a pharmaceutical composition or dosage form, means that at least a portion of the dosage form remains in a subject's stomach following oral administration for about three or more hours, which is substantially longer than the average residence time of a corresponding IR dosage form. While it is retained in the stomach, the dosage form continuously releases the drug.

"Release," "released," and the like, when used in connection with a pharmaceutical composition or dosage form, refers to the portion of the drug substance that leaves the dosage form following contact with an aqueous environment. Unless otherwise indicated, the quantity of drug released from a dosage form is measured by dissolution testing in water (37° C., initial pH of 6.8, using apparatus 2) as described the *United States Pharmacopeia*, 28th Revision, Chapter 711, Second Supplement, (Aug. 1, 2005 to Dec. 31, 2005). The results of the dissolution testing are reported as % (w/w) released as a function of time or as the release time, $t_N$, where N is the % (w/w) of drug released or dissolved. For the purposes of this disclosure, complete drug release occurs when at least 90% of the drug has been released from the dosage form (i.e., at $t_{90}$).

"Steady-state," when used in connection with pharmacokinetic (PK) parameters such as the minimum ($C_{MIN}$) and maximum ($C_{MAX}$) concentrations of the drug substance in the blood plasma of the subject, refers to the approximately constant values of the PK parameters that result from repeated administration of a dosage form at uniform dosing intervals. For dosage forms containing pregabalin, steady-state values of $C_{MAX}$ and $C_{MIN}$ usually occur about 24 to 48 hours following first administration.

A test dosage form is "bioequivalent" to a reference dosage form if the 90% confidence interval estimate for the ratio of the mean value of the total exposure from treatment with the test dosage form to the mean value of the total exposure from treatment with the reference dosage form lies within the range of 80% to 125%. Here, the ratio is expressed as a percentage (100%×test/reference) and the 90% confidence interval is expressed as a percentage of the reference mean. For single-dose studies, the total exposure is the area under the plasma concentration-time curve from time zero (time of dosing) to time infinity; for steady-state studies, the total exposure is the area under the plasma concentration-time curve over the dosing interval. See, U.S. Department of Health and Human Services, Food and Drug Administration, Center for Drug Evaluation and Research, *Guidance for Industry, Bioavailability and Bioequivalence Studies for Orally Administered Drug Products—General Considerations* (Rev. 1, March 2003).

"Poorly soluble" substances are those that are classified as "sparingly soluble," "slightly soluble," "very slightly soluble," or "practically insoluble," i.e., compounds having a solubility of one part of water to about 30-100 parts of water, about 100-1000 parts of water, about 1000-10,000 parts of water, or about 10,000 or greater parts of water, respectively, when measured at room temperature and a pH of 5 to 7.

TABLE 1 lists abbreviations used throughout the specification.

TABLE 1

List of Abbreviations

| Abbreviation | Description |
|---|---|
| ACN | acetonitrile |
| API | active pharmaceutical ingredient |
| aq | aqueous |
| BID | twice daily |
| CAP | cellulose acetate phthalate |
| CAT | cellulose acetate trimellitate |
| CEC | carboxyethylcellulose |
| CMC | carboxymethylcellulose |
| CMEC | carboxymethylethylcellulose |
| $C_{MAX}$ | maximum concentration of API in subject's plasma |
| $C_{MIN}$ | minimum concentration of API in subject's plasma |
| dpm | dips per minute |
| EC | ethyl cellulose |
| ER | extended release |
| Et₃N | triethylamine |
| GABA | γ-aminobutyric acid |
| GI | gastrointestinal |

TABLE 1-continued

List of Abbreviations

| Abbreviation | Description |
|---|---|
| HDPE | high density polyethylene |
| HEC | hydroxyethyl cellulose |
| HPC | hydroxypropylcellulose |
| HPCAP | hydroxypropylcellulose acetate phthalate |
| HPCAS | hydroxypropylcellulose acetate succinate |
| HPLC | high-pressure liquid chromatography |
| HPMC | hydroxypropylmethylcellulose |
| HPMCAP | hydroxypropylmethylcellulose acetate phthalate |
| HPMCAS | hydroxypropylmethylcellulose acetate succinate |
| HPMCAT | hydroxypropylmethylcellulose acetate trimellitate |
| HPMCP | hydroxypropylmethylcellulose phthalate |
| IR | Immediate release |
| kp | kiloponds |
| L, W, H, V | length, width, height, volume |
| MC | methylcellulose |
| Me | methyl |
| Mn | number average molecular weight |
| Mv | molecular weight based on intrinsic viscosity |
| Mw | weight average molecular weight |
| n | number of samples |
| PE | polyethylene |
| PEG | polyethylene glycol |
| PPG | polypropylene glycol |
| PK | pharmacokinetic |
| PVA | polyvinyl alcohol |
| PVAc | polyvinyl acetate |
| PVP | polyvinylpyrrolidone |
| PVPP | polyvinylpolypyrrolidone |
| QD | once daily |
| RH | relative humidity |
| rpm | revolutions per minute |
| RT | room temperature, about 20° C. to 25° C. |
| s | seconds |
| $t_R$ | dosage form retention time in subject's stomach |
| $t_N$ | dosage form drug release (aqueous dissolution) time, where N is % released; N ≥ 90 corresponds to complete release |
| $t_{MAX}$ | time to reach $C_{MAX}$ following administration |
| TID | three times daily |
| USP | United States Pharmacopoeia |
| VA | vinylacetate |
| v/v | volume/total volume × 100, % |
| w/v | weight (g)/total volume (mL) × 100, % |
| w/w | weight (mass)/total weight (mass) × 100, % |

Any reference in this disclosure to a temperature range, a pH range, a weight (mass) range, a molecular weight range, a percent range, etc., whether expressly using the words "range" or "ranges," includes the indicated endpoints and points between the end points.

As noted above, the peroral pharmaceutical composition comprises an active pharmaceutical ingredient (API) and excipients. The active pharmaceutical ingredient includes pregabalin or a pharmaceutically acceptable complex, salt, solvate or hydrate thereof. The API generally comprises from about 5% to about 60% of the pharmaceutical composition by weight, which would typically correspond to a solid dosage form (e.g., tablet) that contains from about 50 mg to about 600 mg of pregabalin. Besides pregabalin, other useful active pharmaceutical ingredients may include those having a similar half-life (e.g., about 9 hours or less) and absorption characteristics in the GI tract.

Pregabalin may be prepared using known methods. In some of these methods, a racemic mixture of 3-aminomethyl-5-methyl-hexanoic acid is synthesized and subsequently resolved into its R- and S-enantiomers. Such methods are described in U.S. Pat. No. 5,563,175 to R. B. Silverman et al., U.S. Pat. No. 6,046,353 to T. M. Grote et al., U.S. Pat. No. 5,840,956 to T. M. Grote et al., U.S. Pat. No. 5,637,767 to T. M. Grote et al., U.S. Pat. No. 5,629,447 to B. K. Huckabee & D. M. Sobieray, and U.S. Pat. No. 5,616,793 to B. K. Huckabee & D. M. Sobieray. In each of these methods, the racemate is reacted with a chiral acid (a resolving agent) to form a pair of diastereoisomeric salts, which are separated by known techniques, such as fractional crystallization and chromatography. In other methods, pregabalin is synthesized directly using a chiral auxiliary, (4R,5S)-4-methyl-5-phenyl-2-oxazolidinone. See, e.g., U.S. Pat. Nos. 6,359,169, 6,028,214, 5,847,151, 5,710,304, 5,684,189, 5,608,090, and 5,599,973, all to Silverman et al. In another method, pregabalin is prepared via asymmetric hydrogenation of a cyano-substituted olefin to produce a chiral cyano precursor of (S)-3-aminomethyl-5-methyl hexanoic acid, which is subsequently reduced to yield pregabalin. See U.S. Patent Application 2003/0212290 A1 to Burk et al.

The pharmaceutical composition may employ any pharmaceutically acceptable form of pregabalin, including its free form (zwitterion), and its pharmaceutically acceptable complexes, salts, solvates, hydrates, and polymorphs. Salts include, without limitation, acid addition salts and base addition salts, including hemisalts. Pharmaceutically acceptable acid addition salts may include nontoxic salts derived from inorganic acids such as hydrochloric, nitric, phosphoric, sulfuric, hydrobromic, hydroiodic, hydrofluoric, phosphorous, and the like, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Potentially useful salts include acetate, aspartate, benzoate, chlorobenzoate, methylbenzoate, dinitrobenzoate, besylate, bicarbonate, carbonate, bisulfate, sulfate, pyrosulfate, bisulfite, sulfite, borate, camsylate, caprylate, citrate, edisylate, esylate, formate, fumarate, gluceptate, gluconate, glucuronate, hexafluorophosphate, hibenzate, hydrochloride, chloride, hydrobromide, bromide, hydroiodide, iodide, isethionate, isobutyrate, lactate, malate, maleate, malonate, mandelate, mesylate, methylsulfate, naphthylate, 2-napsylate, nicotinate, nitrate, orotate, oxalate, palmitate, pamoate, phosphate, hydrogen phosphate, dihydrogen phosphate, metaphosphate, pyrophosphate, phthalate, propionate, saccharate, sebacate, stearate, suberate, succinate, tartrate, tosylate, trifluoroacetate, and the like.

Pharmaceutically acceptable base salts may include nontoxic salts derived from bases, including metal cations, such as an alkali or alkaline earth metal cation, as well as amines. Examples of potentially useful salts include, without limitation, aluminum, arginine, N,N'-dibenzylethylenediamine, calcium, chloroprocaine, choline, diethanolamine, diethylamine, dicyclohexylamine, ethylenediamine, glycine, lysine, magnesium, N-methylglucamine, olamine, potassium, procaine, sodium, tromethamine, zinc, and the like. For a discussion of useful acid and base addition salts, see S. M. Berge et al., *J. of Pharm. Sci.*, 66:1-19 (1977); see also Stahl and Wermuth, *Handbook of Pharmaceutical Salts: Properties, Selection, and Use* (2002).

The pharmaceutically acceptable salts of pregabalin may be prepared by reacting its free (or zwitterionic) form with a desired acid or base; by removing an acid- or base-labile protecting group from a suitable precursor of pregabalin; by ring-opening a suitable cyclic (lactam) precursor using a desired acid or base; or by converting one salt of pregabalin to another by reaction with an appropriate acid or base or by contact with a suitable ion exchange column. All of these transformations are typically carried out in a solvent. The resulting salt may precipitate out and be collected by filtration or may be recovered by evaporation of the solvent. The degree of ionization in the resulting salt may vary from completely ionized to almost non-ionized.

Pregabalin may exist in unsolvated and solvated forms (including hydrates) and in the form of other multi-component complexes in which the drug and at least one additional component is present in stoichiometric or non-stoichiometric amounts. Multi-component complexes (other than salts and solvates) include clathrates (drug-host inclusion complexes) and pharmaceutical co-crystals. The latter are defined as crystalline complexes of neutral molecular constituents that are bound together through non-covalent interactions. Co-crystals may be prepared by melt crystallization, by recrystallization from solvents, or by physically grinding the components together. See, e.g., O. Almarsson & M. J. Zaworotko, *Chem. Comm.* 1889-1896 (2004). For a general review of multi-component complexes, see J. K. Haleblian, *J. Pharm. Sci.* 64(8):1269-88 (1975).

Useful forms of pregabalin include all of its polymorphs and crystal habits, the corresponding R-enantiomer of pregabalin, and various mixtures of pregabalin and the R-enantiomer, including a racemic mixture of pregabalin and the R-enantiomer.

In addition, the pharmaceutical composition may employ prodrugs of pregabalin. Such prodrugs may be prepared by replacing appropriate functional groups of pregabalin with functionalities known as "pro-moieties," as described, for example, in H. Bundgaar, *Design of Prodrugs* (1985). Examples of prodrugs would thus include derivatives of pregabalin in which an ester group replaces the carboxylic acid group or an amide group replaces the amino group.

Useful forms of pregabalin may also include pharmaceutically acceptable isotopically labeled compounds in which one or more atoms are replaced by atoms having the same atomic number, but an atomic mass or mass number different from the atomic mass or mass number that predominates in nature. Examples of isotopes suitable for inclusion in pregabalin include isotopes of hydrogen ($^2$H and $^3$H), carbon ($^{11}$C, $^{13}$C and $^{14}$C), and nitrogen ($^{13}$N and $^{15}$N). Isotopically labeled forms of pregabalin may generally be prepared by techniques known to those skilled in the art.

In addition to the API, the pharmaceutical composition includes various excipients, including a matrix forming agent and a swelling agent. For peroral solid dosage forms (e.g., tablets), the matrix forming agent imparts structural integrity and helps control or extend the rate of drug release, among other functions. The matrix forming agent may comprise about 5% to about 45% of the pharmaceutical composition by weight and often comprises about 20% to about 35% of the pharmaceutical composition by weight.

Useful matrix forming agents include physical mixtures of polyvinyl acetate (PVAc) and polyvinylpyrrolidone (PVP). Polyvinylpyrrolidone (PVP), which is also known as povidone or povidonum, is a homopolymer of 1-vinyl-pyrrolidin-2-one, typically having a molecular weight (Mw) of about $1 \times 10^3$ to about $1 \times 10^7$, about $2.5 \times 10^3$ to about $3 \times 10^6$, or about $1 \times 10^4$ to about $1 \times 10^5$. Polyvinylpyrrolidone is available from BASF under the trade name KOLLIDON® and from ISP under the trade name PLASDONE®. Polyvinyl acetate (PVAc) is a homopolymer of vinyl acetate, typically having a molecular weight (Mw) of about $1 \times 10^5$ to about $1 \times 10^6$. Based on the total weight of PVAc and PVP, the matrix forming agent may comprise from about 0% to about 90% PVAc by weight, from about 20% to about 90% PVAc by weight, from about 40% to about 90% PVAc by weight, from about 60% to about 90% PVAc by weight, from about 70% to about 90% PVAc by weight, or from about 80% to about 90% PVAc by weight. In many cases, the matrix forming agent comprises from about 70% to about 85% PVAc by weight, based on the total weight of PVAc and PVP. A useful matrix forming agent is available from BASF under the trade name KOLLIDON® SR, which is nominally an 80/19 (w/w) mixture of mixture of PVAc and PVP, respectively.

The pharmaceutical composition includes other excipients, including a swelling agent. As its name suggests, the swelling agent absorbs water from the gastric fluid which causes the solid dosage form to expand in size, and may also influence the drug release rate by, for example, creating channels or by forming a hydrocolloid. Swelling agents may be soluble or insoluble in water. The swelling agent may comprise about 5% to about 70% of the pharmaceutical composition by weight, about 10% to about 70% of the pharmaceutical composition by weight, or about 15% to about 70% of the pharmaceutical composition by weight. In many cases, the swelling agent may comprise about 10% to about 55% of the pharmaceutical composition by weight, about 20% to about 55% of the pharmaceutical composition by weight, or about 30% to about 55% of the pharmaceutical composition by weight.

Useful swelling agents include cross-linked homopolymers of 1-vinyl-pyrrolidin-2-one, which are known as crospovidone, crospovidonum, cross-linked povidone, and polyvinylpolypyrrolidone (PVPP). Crospovidones, which are insoluble in water, are available from BASF under the trade names KOLLIDON® CL and KOLLIDON® CL-10 and from ISP under the trade names POLYPLASDONE® XL and POLYPLASDONE® XL-10.

In addition to crospovidones, the swelling agent may include polyethylene oxide (PEO), which is also known as polyoxirane and polyoxyethylene. Polyethylene oxides are homopolymers of ethylene oxide, typically having a molecular weight (Mw) of about $1 \times 10^5$ to about $1 \times 10^7$ or about $1 \times 10^6$ to about $1 \times 10^7$. Polyethylene oxides are supplied in various grades based on molecular weight and are commercially available from Union Carbide under the trade name POLYOX®. When used in conjunction with a crospovidone, the PEO typically comprises from about 5% to about 35% or from about 10% to about 25% of the pharmaceutical composition by weight, and the crospovidone typically comprises from about 10% to about 35% or from about 20% to about 30% of the pharmaceutical composition by weight.

In addition to a matrix forming agent and a swelling agent, the pharmaceutical composition may optionally include a gelling agent, which modifies (e.g. extends) the drug release characteristics of the dosage form. Gelling agents, which are also known as hydrocolloids, include synthetic and naturally occurring polymers that are typically poorly soluble (e.g., slightly soluble to sparingly soluble) in water. When exposed to water, the gelling agent forms a viscous mixture (i.e., viscosity greater than water) that retards diffusion of the drug through the dosage form thereby extending the time for drug release from the dosage form. The gelling agent typically comprises from about 0% to about 25%, from about 5% to about 25%, or from about 5% to about 20% of the pharmaceutical composition based on weight. Useful gelling agents include carbomers, polysaccharides or both.

Carbomers are acrylic acid polymers which are cross-linked with allylsucrose or allyl ethers of penaerythritol and are known variously as carboxy polymethylene, polyacrylic acid, and carboxyvinyl polymers. Carbomers have from about 56% to about 68% carboxy moieties on a dry basis and have number-average molecular weights of about $1 \times 10^5$ to about $1 \times 10^{10}$ or about $7 \times 10^5$ to about $4 \times 10^9$. Carbomers are available from RITA under the trade name ACRITAMER® and from Noveon under the trade names CARBOPOL® and PEMULEN®.

Representative polysaccharides include xanthan gum, inulin, guar gum, chitosan, ceratonia, and carregeenan, either alone or in combination. Xanthan gum, which is also known as corn sugar gum, is a polysaccharide having a molecular weight (Mw) of about $2\times10^6$. The polymer is comprised of a primary chain of β-D-glucose moieties linked by (1→4) glycosidic bonds, as well as trisaccharide side chains, which are attached to alternating glucopyranose moieties. Each of the side chains is comprised of a β-D-glucuronic acid moiety which is linked to a β-D-mannose moiety and an α-D-mannose moiety via (1→4) and (1→2) glycosidic bonds, respectively. The α-D-mannose moiety is linked to the primary chain via a (1→3) glycosidic bond and a majority of the terminal β-D-mannose moieties are linked to pyruvate moieties. Xanthan gum is typically prepared as a sodium, potassium, or calcium salt, and is available in various grades having different particle sizes from CP Kelco under the trade names KELTROL® and XANTURAL®, from Rhodia under the trade name RHODIGEL®, and from R.T. Vanderbilt Company, Inc. under the trade name VANZAN®.

Inulin, which is also known as oligofructose and polyfructose, is a class of naturally occurring polysaccharides comprised of a linear chain of β-D-fructose moieties linked by (2→1) glycosidic bonds, which is usually terminated with a glucose molecule. The number of D-fructose moieties may range from 2 to about 140, but typically ranges from about 25 to about 30. Inulins are available from Sensus Operations CV under the trade name FRUTAFIT®.

Guar gum, which is also known as guar galactomannan, guar flour, and jaguar gum, is a hydrocolloidal polysaccharide having a molecular weight (Mw) of about $2\times10^5$. Guar gum is comprised of a linear chain of β-D-mannose moieties linked by (1→4) glycosidic bonds and having monosaccharide side chains comprised of α-D-galactose moieties linked to the glucopyranose moieties by (1→6) glycosidic bonds. The ratio of β-D-mannose moieties to α-D-galactose moieties generally ranges from about 1:1.4 to about 1:2 and the number-average molecular weight is typically about $2\times10^5$. Guar gun is obtained from natural sources, but synthetic derivatives are also available, including guar acetate, guar phthalate, guar acetate phthalate, oxidized guar gum, and sodium carboxymethyl guar. Guar gum is available in various particles sizes from Aqualon under the trade name GALACTASOL® and from Danisco under the trade names MEYPRO® Guar and MEYPRODOR.

Chitosan is known by a variety of names including chitosan hydrochloride, chitosani hydrochloridum, deacetylated chitin, deactylchitin, poly-β-(1,4)-2-amino-2-deoxy-D-glucose, 2-amino-2-deoxy-(1,4)-β-D-glucopyranan, β-1,4-poly-D-glucosamine, poly-D-glucosamine, and poly-(1,4-β-D-glucopyranosamine). Chitosan is a class of sparingly water-soluble polysaccharides comprised of copolymers of β-D-glucosamine and N-acetyl-β-D-glucosamine, which are prepared by deacetylation and depolymerization of chitin. The extent of deacetylation and depolymerization varies from manufacturer, but deacetylation of about 80% or greater and number-average molecular weights of about $1\times10^4$ to about $1\times10^6$ are typical.

Ceratonia is a naturally occurring polysaccharide which is also known as carob bean gum, carob flour, ceratonia gum, Cheshire gum, locust bean gum, and St. John's bread. Like guar gum, ceratonia is a galactomannan. It is comprised of a primary chain of β-D-mannose moieties linked by (1→4) glycosidic bonds and includes side chains comprised of single β-D-galactose moieties which are linked to every fourth or fifth D-mannopyranose moiety by (1→6) glycosidic bonds. The molecular weight (Mw) of Ceratonia may range from about $5\times10^4$ to about $3\times10^6$ and is available in various particle sizes from Danisco under the trade names GRINDSTED®LBG and MEYPRO® LBG.

Carregeenan, which is also known as Chondrus extract and Irish moss extract, is a hydrocolloid polysaccharide comprised primarily of potassium, sodium, calcium, magnesium, or ammonium sulfate esters of D-galactose and 3,6-anhydro-D-galactose copolymers. The pyranose moieties are linked by alternating a (1→3) and β (1→4) glycosidic bonds. There exist at least three types of carregeenan, known as λ-carrageenan, ι-carrageenan, and κ-carrageenan, which differ in the amounts of sulfate ester and 3,6-anhydrogalactopyranose moieties. Lambda-carrageenan is a non-gelling polymer which contains about 35% sulfate ester groups by weight and no 3,6-anhydrogalactose moieties; t-carrageenan is a gelling polymer which contains about 32% sulfate ester groups by weight and about 30% 3,6-anhydrogalactose moieties; and κ-carrageenan is a comparatively stronger (i.e., inelastic, brittle or firm) gelling polymer which contains about 25% sulfate ester moieties by weight and about 34% 3,6-anhydrogalactose moieties. Carrageenan is available in a number of grades based on gelling type, aqueous solubility, and viscosity when blended with water and can be obtained from FMC Corporation under the trade names GELCARIN®, VISCARIN® and SEASPEN®.

Other useful polysaccharides include cellulosic derivatives which exhibit aqueous solubility over at least a portion of the pH range of 1 to 8, inclusive. Useful polymers thus include ionizable and nonionizable cellulosic polymers, including those having ether or ester or ether and ester substituents and copolymers thereof, including so-called "enteric" and "non-enteric" polymers.

Exemplary ionic cellulosic polymers include carboxymethylcellulose (CMC) and its sodium or calcium salts; carboxyethylcellulose (CEC); carboxymethylethylcellulose (CMEC); hydroxyethylmethylcellulose acetate phthalate; hydroxyethylmethylcellulose acetate succinate; hydroxypropylmethylcellulose phthalate (HPMCP); hydroxypropylmethylcellulose succinate; hydroxypropylcellulose acetate phthalate (HPCAP); hydroxypropylcellulose acetate succinate (HPCAS); hydroxypropylmethylcellulose acetate phthalate (HPMCAP); hydroxypropylmethylcellulose acetate succinate (HPMCAS); hydroxypropylmethylcellulose acetate trimellitate (HPMCAT); hydroxypropylcellulose butyrate phthalate; carboxymethylethylcellulose and its sodium salt; cellulose acetate phthalate (CAP); methylcellulose acetate phthalate; cellulose acetate trimellitate (CAT); cellulose acetate terephthalate; cellulose acetate isophthalate; cellulose propionate phthalate; cellulose propionate trimellitate; cellulose butyrate trimellitate; and mixtures thereof. The ionic cellulosic polymers are available from numerous commercial suppliers. For example, sodium CMC may be obtained from Hercules under the trade names AQUALON® and BLONASE® in various grades based on particle size and degree (e.g., about 0.7 to about 1.2) of carboxymethyl-substitution of the anhydroglucose units.

Exemplary nonionic cellulosics include methylcellulose (MC); ethyl cellulose (EC); hydroxyethyl cellulose (HEC); hydroxypropylcellulose (HPC); hydroxypropylmethylcellulose (HPMC); hydroxypropylmethylcellulose acetate; hydroxyethylmethylcellulose; hydroxyethylcellulose acetate; hydroxyethylethylcellulose; and mixtures thereof. The nonionic cellulosics are available from a variety of commercial sources. For example, MC may be obtained from the Dow Chemical Company under the trade name METHOCEL® A, which has about 27.5% to about 31.5% methoxy groups per anhydroglucose unit based on weight; HPC may be obtained from Hercules under the trade name KLUCEL® in various grades (e.g., EF, EXF, LF, JF, GF, MF, HF, and HXF) having molecular weights ranging from about $8 \times 10^4$ to about $1.2 \times 10^6$ (Mw); HEC may be obtained from Hercules under the trade name NATROSOL® 250 in various grades (e.g., L, G, M, H, H, and HHX) having molecular weights ranging from about $9 \times 10^4$ to about $1.3 \times 10^6$ (Mv); HPMC may be obtained from Hercules under the trade name BENECEL® in various grades (e.g., MP 843, MP 814, MP 824, MP 844, and MP 874) based on aqueous viscosity and from the DOW Chemical Company under trade name METHOCEL®, in various grades (e.g., E, F, J, K and 310) having about 18% to about 29% and about 5% to about 27% methoxy and 2-hydroxypropoxy groups per anhydroglucose unit based on weight, respectively.

The pharmaceutical composition may optionally include one or more lubricants, which aid in various processing steps including component blending and tableting. When present, the lubricants typically comprise from about 0.5% to about 2% of the pharmaceutical composition based on weight. Representative lubricants include talc, stearic acid and its metal salts, including calcium stearate, magnesium stearate, and zinc stearate; stearic acid esters, including polyoxyethylene stearate, glyceryl monostearate, glyceryl palmitostearate, and the like; glyceryl behenate (e.g., COMPRITOL®, which is available from Gattefosse Inc.), sodium lauryl sulfate, hydrogenated vegetable oil, mineral oil, poloxamers (copolymers of ethylene oxide and propylene oxide), polyethylene glycol, sodium chloride, and mixtures thereof.

The pharmaceutical composition may include other excipients, such diluents or fillers, which comprise from about 0% to about 30% of the composition by weight. Diluents may improve the flow characteristics of the pharmaceutical composition during component blending and tableting and may enhance the physical properties of tablets, providing, for example, increased compression strength or hardness, decreased friability, and so on. Representative diluents include monosaccharides, disaccharides, polyhydric alcohols, and mixtures thereof, such as dextrose, lactose monohydrate, spray-dried lactose monohydrate, anhydrous lactose, sucrose, mannitol, spray-dried mannitol, xylitol, and sorbitol. Other useful diluents may include microcrystalline cellulose, starch, pregelatinized starch, dihydrous calcium phosphate, anhydrous dicalcium phosphate, and mixtures thereof.

To prepare the drug product, the components of the pharmaceutical composition are typically dry blended using, e.g., a v-cone blender. The resulting mixture is subsequently compacted in a press to yield individual (unit) dosages (tablets). To improve product homogeneity, the components may be combined and blended in stages. For example, the API may be granulated with one or more of the components by, e.g., fluid bed or extrusion granulation, and then blended with the remaining components. Similarly, the API may be first dry blended with one or more matrix forming agents, while other excipients, such as swelling agents, gelling agents, diluents, lubricants, and the like, may be subsequently admixed in one or more blending operations. If desired, prior to blending one or more of the components may be sized by screening or milling or both. To prepare the final drug product, the compressed dosage forms may undergo further processing, such as polishing, coating, and the like. For a discussion of dry blending, wet and dry granulation, milling, screening, tableting, coating, and the like, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets*, Vol. 1-3 (2d ed., 1990); and D. K. Parikh & C. K. Parikh, *Handbook of Pharmaceutical Granulation Technology*, Vol. 81 (1997).

The pharmaceutical composition is ingested whole and begins to swell or expand when it contacts the gastric fluid (water) in the subject's stomach. The dosage form may have any shape, and includes disk- or oval-shaped tablets defined by a pair of circular or elliptical convex or planar surfaces which are connected by a continuous, substantially flat lateral surface; polygonal-shaped (e.g., triangular, quadrangular, pentagonal, hexagonal, etc.) tablets which have rounded corners and edges and are defined by a pair of convex or planar multi-sided surfaces (e.g., triangles, quadrilaterals, pentagons, hexagons, etc.) that are connected by substantially flat lateral surfaces; and cylindrical-shaped tablets having hemispherical or hemispheroidal ends and having circular or elliptical cross-sections.

The QD dosage form may be retained in the stomach by size exclusion, by dosing with a meal, by dosing before bedtime, or by some combination of these mechanisms. For retention via size exclusion alone, the dosage form expands to a size that prevents it from exiting the stomach through the pylorus. Since the average diameter of the pylorus in an adult is about 13 mm, the size of the dosage form following expansion would range from about 13 mm to about 20 mm or larger, from about 15 mm to about 20 mm or larger, or from about 17 mm to about 20 mm or larger. Here, the "size" of the dosage form corresponds to the largest linear dimension of a cross-section of the dosage form having the smallest area. For example, the size of a disk-shaped tablet corresponds to its diameter and the size of a cylindrical-shaped tablet corresponds to the diameter of its circular cross-section or to the long axis of its elliptical cross-section.

To achieve QD dosing, the dosage form is retained in the stomach for several hours (e.g., $t_R \geq 3$, 4, 5 or 6 hours) and releases pregabalin over an extended period of time (e.g., $t_{90} > 10$, 11, 12, 13, 14, 15, 16, 17, 18, 19 or 20 hours). The dosage form is typically retained in the subject's stomach for a period of time that ranges from about 3 hours to about 11 hours ($3 \leq t_R \leq 11$), from about 6 hours to about 14 hours ($6 \leq t_R \leq 14$), or from about 8 hours to about 14 hours ($8 \leq t_R \leq 14$), and it releases pregabalin over a period of time that ranges from about 12 hours to about 16 hours ($12 \leq t_{90} \leq 16$), from about 12 hours to about 18 hours ($12 \leq t_{90} \leq 18$), from about 12 hours to about 20 hours ($12 \leq t_{90} \leq 20$), from about 14 hours to about 20 hours ($14 \leq t_{90} \leq 20$), or from about 16 hours to about 20 hours ($16 \leq t_{90} \leq 20$). As described in the PK simulations in the Examples below, QD dosage forms that release pregabalin over a period of time that is about 4 hours to about 6 hours longer than the time the dosage form is retained in the stomach appear to minimize variability among patients.

Because eating delays gastric emptying and sleeping decreases GI motility, the dosage form may be administered once daily after a meal or before bedtime (e.g., within about one hour of sleep). To take advantage of both effects and to further prolong drug release, the QD dosage form may be taken after the last meal before bedtime (e.g., after an evening meal). For QD dosage forms taken with a meal or taken before bedtime or taken with a meal and before bedtime, the dosage form may be retained in the stomach with little or no size expansion. In such cases, for example, the size of the dosage form following expansion may be about 9 mm or more.

During any 24-hour period, the QD dosage form achieves a steady-state $C_{MAX}$ that is about equal to or less than the steady-state $C_{MAX}$ of a corresponding immediate release formulation of the API that is taken two- or three-times daily. Likewise, the QD formulation ideally achieves a steady-state $C_{MIN}$ that is about equal to or greater than the steady-state $C_{MIN}$ of the IR formulation that is taken two- or three-times daily. An IR formulation containing 300 mg of pregabalin, which is taken twice daily, exhibits an average steady-state $C_{MAX}$ of about 8.9 μg/mL and an average steady-state $C_{MIN}$ of about 2.8 μg/mL, and an IR formulation containing 150 mg of pregabalin, which is taken twice daily, exhibits an average steady-state $C_{MAX}$ of about 4.4 μg/mL and an average steady-state $C_{MIN}$ of about 1.4 μg/mL. A QD formulation containing pregabalin would ideally achieve an average steady sate $C_{MAX}$ of about 9 μg/mL or less and an average steady-state $C_{MIN}$ of about 0.7 μg/mL or greater.

EXAMPLES

The following examples are intended to be illustrative and non-limiting. Unless otherwise indicated, the following procedures are used to measure drug release (aqueous dissolution), swelling, rigidity, and stability of the drug product as a function of time.

Drug Product Dissolution

The amount of API released from drug product samples immersed in aqueous dissolution media (0.06 N HCl or 0.5 M acetate buffer) at 37° C. is measured using a USP Apparatus 2 (paddles) or Apparatus 3 (reciprocating cylinder), which are operated at 50 rpm or 5 dpm, respectively. Samples of the dissolution media (1 mL) are typically taken at 1, 2, 4, 6, 9, 12, 16, and 24 hours and are analyzed using HPLC under the following conditions: column: Zorbax SB-CN, 150 mm×4.6 mm, 5 μm particle size; column temperature: 23° C.; detector wavelength: 210 nm; flow rate 1 mL/min; injection volume: 25 μL; mobile phase composition: 0.05 M sulfonic acid/ hexane and 2 mL $Et_3N$; pH adjusted to 3.1 with orthophosphoric acid:ACN (880:130); run time: 8 min.

Drug Product Swelling

The increase in the size of the drug product as a function of time following immersion in 0.06 N HCl aq dissolution media is carried out using a USP Apparatus 2 (paddles). Samples of the drug product are periodically withdrawn from the dissolution media and their dimensions measured using calipers.

Drug Product Rigidity

Samples of the drug product are placed in a USP Apparatus 2 (paddles) containing 0.06 N HCl aq dissolution media. Samples of the drug product are periodically withdrawn and their rigidity measured using a texture analyzer (TA 132) with the following settings: 5 kg load cell; TA-8 ¼" ball probe; 0.5 g trigger force; 0.2 mm/s test speed; 10 points/s acquisition rate; 10 mm distance.

Drug Product Stability

Stability testing is carried out by placing samples of the drug product in open HDPE bottles or induction-sealed HDPE bottles, which are stored at 40° C. and 75% relative humidity. Samples of the drug product are pulled at various time intervals—e.g., at 2 weeks for initial screening and at 3 weeks, 6 weeks, or 3 months for subsequent testing—and analyzed for pregabalin content (%, w/w) and lactam content (%, weight of lactam/initial weight of pregabalin) using HPLC.

Examples 1 to 11

TABLES 2 and 3 show compositions of laboratory-scale batches (25 g) containing pregabalin and various excipients; TABLES 4 and 5 show results of drug release as a function of time. For each of the formulations, drug product was prepared by blending all of the tablet components except for magnesium stearate in a TURBULA® mixer for about 15 minutes. Magnesium stearate was passed through a #20 standard sieve and combined with the contents of the TURBULA® mixer using a spatula. The resulting coarse blend was subsequently mixed in the TURBULA® mixer for an additional 4 minutes to obtain a final blend. Each of the final blends was compacted in a CARVER® Press using a compression force of 3000 pounds (EXAMPLES 1 to 5) or 2000 pounds (EXAMPLES 6 to 11) and a dwell time of 0.1 min, resulting in tablets with average hardness values of about 30 kp and nominal tablet weights of 1 g and 1.125 g, respectively. For some of the formulations (EXAMPLES 1 to 5), pregabalin was coated with COMPRITOL® 888 by high-shear granulation prior to blending with the other excipients.

Examples 12 to 14

TABLE 6 shows compositions of laboratory-scale batches (100 g) which contain pregabalin and excipients, and TABLE 7 shows drug release as a function of time. For each of the compositions, drug product was prepared by first combining pregabalin with COMPRITOL® 888 in an extruder-granulator. With the exception of magnesium stearate, the remaining tablet components were blended with the resulting pregabalin granules in a 1-pint V-blender for about 15 minutes. Magnesium stearate was passed through a #20 standard sieve and was combined with the contents of the V-blender using a spatula. The resulting coarse blend was subsequently mixed in the V-blender for an additional 4 minutes to obtain a final blend. Each of the final blends was compressed using a simulated KORSCH® XL 400 press (i.e., PRESSTER® Compaction Simulator) employing an average compression force of about 21 kN and average dwell time of 12 msec. The tablets displayed an average hardness of about 20 kp and a nominal tablet weight of about 1 g.

Examples 15 to 23

TABLE 8 shows compositions of laboratory-scale batches which contain pregabalin and excipients; TABLE 9 shows lactam formation as a function of time. Each of the formulations was made using a process similar to that described above in EXAMPLES 12 to 14.

Examples 24 to 30

TABLE 10 shows compositions of laboratory-scale batches (up to 4 kg) which contain pregabalin and excipients; TABLE 11 shows drug release as a function of time; TABLES 12 and 13 show tablet swelling and changes in tablet rigidity following immersion in an aqueous solution; and TABLE 14 shows lactam formation as a function of time. Drug products for some of the compositions (EXAMPLES 25 to 29) were made using processes similar to those described in EXAMPLES 12 to 14.

Drug product for EXAMPLE 24 was prepared by blending all of the tablet components except magnesium stearate in a 16-quart V-blender for 15 minutes. Magnesium stearate was passed through a #30 standard sieve and was combined with the contents of the V-blender using a spatula. The resulting coarse blend was subsequently mixed in the V-blender for an additional 5 minutes to obtain a final blend. The final blend was compressed in a MANESTY® Betapress using a diamond-shaped (quadrilateral) punch (0.6299"×0.748", 0.0700" cup depth, 0.0040" land) and a triangle-shaped punch (0.6665"×0.6906", 0.0600" cup depth, 0.0040" land). For diamond-shaped tooling, an average tablet hardness of 8.6 kp was obtained for 10 tablets at a pre-compression force setting of about 2.1 kN and a lower main compression setting of about 36 kN. For triangle-shaped tooling, an average tablet hardness of 9.0 kp was obtained for 10 tablets at a pre-compression force setting of about 2.2 kN and a lower main compression setting of about 39.8 kN. The loss in weight upon friability testing was 0.3% for the diamond-shaped tablets and 0.2% for the triangle-shaped tablets, respectively.

Tablets prepared using the MANESTY® Betapress (EXAMPLE 24) exhibited substantially lower tablet hardness than those prepared in previous examples. As a result, the magnesium stearate content of the composition was reduced from 1% to 0.5% to improve tablet hardness (EXAMPLE 30). Drug product was prepared in a manner similar to EXAMPLE 24, except the batch size was reduced from 4 kg to 2 kg and the blending time following magnesium stearate addition was reduced to 4 minutes. The final blend was compressed on the MANESTY® Betapress using the triangle tooling. At a pre-compression force setting of 2.8 kN and lower main compression force setting of 41.5 kN, the tablets had an average (n=10) hardness of 15.2 kp and exhibited 0% weight loss in friability testing. When the pre-compression force setting and the lower main compression force setting were changed to 3.1 kN and 33.2 kN, respectively, the tablets had an average (n=10) hardness of 12.1 kp and exhibited a 0.07% weight loss in friability testing.

Example 31

TABLE 15 shows simulated steady-state minimum ($C_{MIN}$) and maximum ($C_{MAX}$) plasma concentrations of pregabalin, as well as time to $C_{MAX}$ ($t_{MAX}$), for QD pharmaceutical compositions that contain 600 mg of pregabalin. The compositions are retained in the stomach for $t_R$=3, 5, 8, or 10 hours and have total dissolution times $t_{100}$=6, 8, 10, 12, or 16 hours. For comparison purposes, TABLE 15 also shows steady-state PK parameters for an IR pharmaceutical composition containing 300 mg of pregabalin which is dosed twice daily.

The PK simulations are based on a QD dosage form having a normalized dissolution profile provided in TABLE 16. In addition, the PK simulation shown in TABLE 15 assumes that (1) the pharmaceutical composition remains in the stomach the specified time period ($t_R$) for each simulation; (2) the total effective absorption time (window) is 6 hours—the average absorption window for the small intestine and the ascending portion of the colon of the time in the stomach—plus $t_R$; (3) the absorption rate in the lower portion of the small intestine is similar to the upper portion; and (4) the effect of taking the pharmaceutical composition with food, at bedtime, or with food and at bedtime, has no effect on the absorption rate. Food has been shown to delay $t_{MAX}$ of IR formulations, but does not appear to affect the extent of drug absorption. Sleep, however, will likely decrease the rate of drug absorption so that the simulations may underestimate the delay in $t_{MAX}$.

As noted above, the results in TABLE 15 are based on an average absorption window associated with an IR formulation of 6 hours—PK profiles of individual patients receiving the QD dosage could differ. Indeed, PK simulations for a QD dosage form containing 600 mg of pregabalin and exhibiting a $t_{100}$ of 12 hours and a $t_R$ of 5 hours and in which $t_R$ varies from 3.4 hours to 7.7 hours suggests that a $t_{100}$ (or $t_{90}$) approximately 4 to 6 hours longer than $t_R$ reduces variability among subjects.

Example 32

A single-dose pharmacokinetic study was performed to assess the performance of the QD formulation of EXAMPLE 30. The QD dosage form was given (1) in the fasted state, (2) following a high fat breakfast (morning treatment), and (3) following a high fat supper (evening treatment) in accordance with guidelines established by the U.S. Food and Drug Administration. See, U.S. Department of Health and Human Services, Food and Drug Administration, Center for Drug Evaluation and Research, *Guidance for Industry, Food-Effect Bioavailability and Fed Bioequivalence Studies* (December 2002). Here, "high-fat" means that approximately 50 percent of the total caloric content of the meal was derived from fat. The pharmacokinetic results of these three treatments were compared to the results obtained for an identical dose (300 mg) of an immediate release formulation (capsule) comprised of pregabalin, lactose monohydrate, maize starch, and talc.

Based on pregabalin $C_{MAX}$ and $t_{MAX}$ values, peak exposure was lower and occurred later for all three QD formulation treatments relative to the IR capsule, indicating a slower rate of absorption from the QD formulation. Mean $t_{MAX}$ for the QD formulation was about 4 hours for the fasted treatment, more than 2-fold later than the mean $t_{MAX}$ of 1.5 hours for the IR capsule. Following administration of a high-fat meal, $t_{MAX}$ for the QD formulation increased to approximately 10 hours (9.7 hours for the morning treatment and 10.7 hours for evening treatment). Based on mean area under the plasma concentration-time curve from time zero to time infinity, total pregabalin exposure for the QD formulation fasted was less than half of that for the IR capsule. However, when the QD formulation was administered following a high-fat meal, total pregabalin exposures for both the morning and evening treatments were similar to that from the IR capsule. The total exposure achieved when the QD formulation was administered after a high-fat meal was bioequivalent to the IR formulation and should achieve an acceptable profile for once daily dosing.

It should be noted that, as used in this specification and the appended claims, singular articles such as "a," "an," and "the," may refer to one object or to a plurality of objects unless the context clearly indicates otherwise. Thus, for example, reference to a composition containing "a compound" may include a single compound or two or more compounds.

It is to be understood that the above description is intended to be illustrative and not restrictive. Many embodiments will be apparent to those of skill in the art upon reading the above description. The scope of the invention should, therefore, be determined with reference to the appended claims, along with the full scope of equivalents to which such claims are entitled. The disclosures of all articles and references, including patents, patent applications and publications, are incorporated herein by reference in their entirety and for all purposes.

TABLE 2

Pharmaceutical compositions containing pregabalin (% w/w) - EXAMPLES 1 to 5

| Component | 1 | 2 | 3 | 4 | 5 |
|---|---|---|---|---|---|
| Pregabalin | 30.0 | 30.0 | 30.0 | 30.0 | 30.0 |
| KOLLIDON ® SR | 31.7 | 31.7 | 31.7 | 41.7 | 41.7 |
| PLASDONE ® XL | 15.0 | 15.0 | 15.0 | 15.0 | 15.0 |
| GELCARIN ® GP812 | 15.0 | | | 5.0 | |
| GELCARIN ® GP911 | | 15.0 | | | |
| VISCARIN ® GP109 | | | 15.0 | | 5.0 |
| COMPRITOL ® 888 | 7.8 | 7.8 | 7.8 | 7.8 | 7.8 |
| Magnesium stearate | 0.5 | 0.5 | 0.5 | 0.5 | 0.5 |
| Total | 100.0 | 100.0 | 100.0 | 100.0 | 100.0 |

TABLE 3

Pharmaceutical compositions containing pregabalin (% w/w)- EXAMPLES 6 to 11

| Component | 6 | 7 | 8 | 9 | 10 | 11 |
|---|---|---|---|---|---|---|
| Pregabalin | 26.7 | 26.7 | 26.7 | 26.7 | 26.7 | 26.7 |
| KOLLIDON ® SR | 40.0 | 40.0 | 30.0 | 30.0 | 37.3 | 30.0 |
| PLASDONE ® XL | 20.0 | 25.0 | 20.0 | 25.0 | 25.0 | 28.0 |
| POLYOX ® WSR Coagulant | 12.3 | 7.3 | 22.3 | 17.3 | 10.0 | 14.3 |
| Magnesium stearate | 1.0 | 1.0 | 1.0 | 1.0 | 1.0 | 1.0 |
| Total | 100.0 | 100.0 | 100.0 | 100.0 | 100.0 | 100.0 |

TABLE 4

Pregabalin release (% w/w) as a function of time (hours) - EXAMPLES 1 to 5

| Time | 1 | 2 | 3 | 4 | 5 |
|---|---|---|---|---|---|
| 0.0 | 0.0 | 0.0 | 0.0 | 0.0 | 0.0 |
| 0.5 | 16.7 | 15.0 | 10.8 | 51.6 | 39.0 |
| 2.0 | 35.5 | 31.4 | 26.1 | 84.0 | 63.5 |
| 4.0 | 48.4 | 43.2 | 39.1 | 96.8 | 76.6 |
| 6.0 | 56.8 | 52.1 | 48.9 | 101.0 | 85.0 |
| 9.0 | 66.9 | 63.2 | 60.5 | 101.4 | 92.8 |
| 12.0 | 75.7 | 72.9 | 69.6 | 101.4 | 98.0 |

Measurements carried out at 37° C. using a USP 3 apparatus containing 0.06N HCl aq.
Each of the release data for Examples 1-3 is an average of two samples; release data for Examples 4 and 5 are for single samples.

TABLE 5

Pregabalin release (% w/w) as a function of time (hours)- EXAMPLES 6 to 11

| Time | 6 | 7 | 8 | 9 | 10 | 11 |
|---|---|---|---|---|---|---|
| 0.0 | 0.0 | 0.0 | 0.0 | 0.0 | 0.0 | 0.0 |
| 0.5 | 17.4 | 31.1 | 13.2 | 15.8 | 16.4 | 20.6 |
| 1.0 | 25.7 | 43.7 | 27.2 | 32.6 | 35.6 | 43.1 |
| 2.0 | 36.0 | 58.1 | | | | |
| 4.0 | 50.5 | 74.8 | 40.9 | 47.4 | 50.9 | 59.5 |
| 6.0 | | | 52.6 | 59.4 | 62.6 | 70.3 |
| 8.0 | 70.1 | 92.3 | | | | |
| 9.0 | | | 66.9 | 73.6 | 76.0 | 82.0 |
| 12.0 | 83.0 | 101.4 | 78.7 | 84.5 | 85.5 | 90.3 |
| 16.0 | 91.8 | 107.2 | | | | |
| 20.0 | 98.5 | 109.2 | | | | |
| 24.0 | 103.4 | 109.2 | | | | |

Measurements carried out at 37° C. using a USP 3 apparatus containing 0.05M aq acetate buffer (pH 4.5).
Each of the release data for Examples 8-11 is an average of 2 samples; release data for Examples 6 and 7 are for single samples.

TABLE 6

Pharmaceutical compositions containing pregabalin (% w/w) - EXAMPLES 12 to 14

| Component | 12 | 13 | 14 |
|---|---|---|---|
| Pregabalin | 30.0 | 30.0 | 30.0 |
| KOLLIDON ® SR | 51.7 | 49.7 | 46.7 |
| PLASDONE ® XL | 10.0 | 12.0 | 15.0 |
| COMPRITOL ® 888 | 7.8 | 7.8 | 7.8 |
| Magnesium stearate | 0.5 | 0.5 | 0.5 |
| Total | 100.0 | 100.0 | 100.0 |

TABLE 7

Pregabalin release (% w/w) as a function of time (hours) - EXAMPLES 12 to 14

| Time | 12 | 13 | 14 |
|---|---|---|---|
| 0.0 | 0.0 | 0.0 | 0.0 |
| 0.5 | 42.2 | 34.7 | 47.0 |
| 2.0 | 67.5 | 58.2 | 88.9 |
| 4.0 | 82.8 | 75.1 | 105.2 |
| 6.0 | 91.5 | 86.2 | 111.9 |
| 9.0 | 98.8 | 96.1 | 112.9 |
| 12.0 | 101.8 | 102.2 | 112.9 |

Measurements carried out at 37° C. using a USP 3 apparatus containing 0.06N HCl aq.
Each of the release data for Examples 12-14 is an average of 2 samples.

TABLE 8

Pharmaceutical compositions containing pregabalin (% w/w) - EXAMPLES 15 to 23

| Component | 15 | 16 | 17 | 18 | 19 | 20 | 21 | 22 | 23 |
|---|---|---|---|---|---|---|---|---|---|
| Pregabalin | 30.0 | 30.0 | 30.0 | 30.0 | 30.0 | 30.0 | 30.0 | 30.0 | 30.0 |
| KOLLIDON ® SR | 22.0 | 34.5 | 42.0 | 27.0 | 39.5 | 50.0 | 61.5 | 45.0 | 29.5 |
| PLASDONE ® XL | 20.0 | 17.5 | 10.0 | 20.0 | 15.0 | 12.0 | 8.0 | 12.0 | 15.0 |
| POLYOX ® WSR Coagulant | 20.0 | 17.5 | | | | | | | |
| CARBOPOL ® 71G | | | | | | | | 5.0 | |
| VISCARIN ® GP109 | | | | 15.0 | 15.0 | | | | |
| NATROSOL ® 250 | | | 17.5 | | | | | | 17.5 |
| COMPRITOL ® 888 | 7.5 | | | 7.5 | | 7.5 | | 7.5 | 7.5 |
| Magnesium stearate | 0.5 | 0.5 | 0.5 | 0.5 | 0.5 | 0.5 | 0.5 | 0.5 | 0.5 |
| Total | 100.0 | 100.0 | 100.0 | 100.0 | 100.0 | 100.0 | 100.0 | 100.0 | 100.0 |

TABLE 9

Lactam formation (%, weight of lactam/initial weight of pregabalin)

| Example | Initial | 2 Weeks |
|---|---|---|
| 15 | 0.005 | 0.008 |
| 16 | 0.006 | 0.007 |
| 17 | 0.011 | 0.012 |
| 18 | 0.009 | 0.011 |
| 19 | 0.015 | 0.033 |
| 20 | 0.099 | 0.010 |
| 21 | 0.016 | 0.011 |
| 22 | 0.012 | 0.018 |
| 23 | 0.010 | 0.014 |

All samples stored in open bottles at 40° C. and 75% RH except for Example 19, which was stored in a closed bottle.

TABLE 10

Pharmaceutical compositions containing pregabalin (% w/w) - EXAMPLES 24 to 30

| Component | 24 | 25 | 26 | 27 | 28 | 29 | 30 |
|---|---|---|---|---|---|---|---|
| Pregabalin | 26.7 | 26.7 | 26.7 | 26.7 | 26.7 | 26.7 | 26.7 |
| KOLLIDON ® SR | 22.3 | 22.3 | 19.3 | 9.3 | 25.3 | | 22.8 |
| PLASDONE ® XL | 25.0 | 25.0 | 25.0 | 25.0 | 23.5 | | 25.0 |
| POLYOX ® WSR N60K NF | 20.0 | | | | | | 20.0 |
| POLYOX ® WSR Coagulant | | 10.0 | 10.0 | 10.0 | 23.5 | | |
| POLYOX ® WSR 303 | | | | | | 51.7 | |
| CARBOPOL ® 71G | 5.0 | | | | | | 5.0 |
| HEC 250 HHX | | 15.0 | 18.0 | 18.0 | | | |
| METHOCEL ® K15M | | | | | | 14.5 | |
| METHOCEL ® E5 | | | | | | 6.1 | |
| Mannitol | | | | | | 10.0 | |
| Magnesium stearate | 1.0 | 1.0 | 1.0 | 1.0 | 1.0 | 1.0 | 0.5 |
| Total | 100.0 | 100.0 | 100.0 | 100.0 | 100.0 | 100.0 | 100.0 |

TABLE 11

Pregabalin release (% w/w) as a function of time (hours) - EXAMPLES 24 to 30

| Time | 24 | 25 | 26 | 27 | 28 | 29 | 30 |
|---|---|---|---|---|---|---|---|
| 0 | 0.0 | 0.0 | 0.0 | 0.0 | 0.0 | 0.0 | 0.0 |
| 1 | 18.6 | 22.1 | 21.3 | 22.5 | 18.1 | 9.3 | 18.4 |
| 2 | 29.5 | 31.7 | 31.0 | 32.8 | 27.3 | 16.8 | 28.6 |
| 4 | 43.9 | 45.7 | 45.0 | 47.3 | 41.9 | 29.2 | 44.0 |
| 6 | 55.6 | 55.1 | 55.5 | 59.7 | 54.2 | 39.4 | 55.8 |
| 8 | | | | | 64.5 | 52.2 | |
| 9 | 70.7 | 69.3 | 68.6 | 73.9 | | | 69.1 |
| 10 | | | | | 73.2 | 56.9 | |
| 12 | 82.3 | 78.0 | 78.4 | 84.5 | 80.8 | 64.5 | 79.6 |
| 16 | 92.8 | 88.2 | 88.6 | 94.7 | | | 90.2 |
| 20 | 102.7 | 96.2 | | | | | |
| 24 | 106.8 | 99.3 | 99.0 | 103.6 | | | 100.4 |

Measurements carried out at 37° C. using a USP 2 apparatus containing 0.06N HCl aq.

TABLE 12

Tablet dimensions (L, H, W in mm) and volume (V in mm$^3$) as a function of time (hours) - EXAMPLES 24 & 30

| | 24 | | | | 30 | | | |
|---|---|---|---|---|---|---|---|---|
| Time | L | W | H | V | L | W | H | V |
| 0 | 19.19 | 10.93 | 7.80 | 1637.23 | 17.10 | 17.70 | 6.71 | 1014.86 |
| 2 | 21.06 | 12.06 | 11.42 | 2901.99 | 19.80 | 20.14 | 10.42 | 2077.80 |
| 4 | 22.59 | 13.54 | 12.55 | 3837.94 | 20.78 | 20.92 | 10.66 | 2318.58 |
| 6 | 22.80 | 13.18 | 12.97 | 3896.89 | 21.43 | 21.34 | 11.59 | 2648.90 |
| 9 | 23.93 | 13.93 | 13.84 | 4616.32 | 17.10 | 17.70 | 6.71 | 1014.86 |

TABLE 13

Rigidity (g · mm) as a function of time (hours) - EXAMPLES 24 & 30

| Time | 24 | 30 |
|---|---|---|
| 0 | | |
| 2 | 4446.84 | |
| 4 | 3004.47 | 1902.92 |
| 6 | 1759.25 | 1131.43 |
| 9 | 1129.57 | |

TABLE 14

Pregabalin (% w/w) and corresponding lactam content (% based on weight of pregabalin) as a function of time - EXAMPLES 25 to 30

| Time | 25 | 30 |
|---|---|---|
| Initial | 0.00 | 0.01 |
| 3 weeks | 0.03 | 0.02 |
| 6 weeks | 0.01 | 0.03 |
| 3 months | 0.06 | 0.09 |

TABLE 15

Simulated steady-state PK parameters for IR and QD dosage forms containing pregabalin

| $t_R$ hours | $t_{100}$ hours | $C_{MAX}$ µg/mL | $C_{MIN}^1$ µg/mL | $t_{MAX}^2$ hours |
|---|---|---|---|---|
| IR Dosage Form[3] | | | | |
| — | — | 8.85 | 2.80 | 0.75 |
| QD Dosage Forms[4] | | | | |
| 3 | 6 | 9.73 | 1.48 | 6.0 |
| 3 | 8 | 8.76 | 1.62 | 8.0 |
| 3 | 10 | 7.67 | 1.57 | 9.0 |
| 3 | 12 | 6.77 | 1.38 | 9.0 |
| 3 | 16 | 5.81 | 1.18 | 9.0 |
| 5 | 6 | 9.73 | 1.48 | 6.0 |
| 5 | 8 | 8.76 | 1.62 | 8.0 |
| 5 | 10 | 7.89 | 1.79 | 10.0 |
| 5 | 12 | 6.93 | 1.75 | 8.0 |
| 5 | 16 | 5.92 | 1.44 | 8.4 |
| 8 | 6 | 9.73 | 1.48 | 6.0 |
| 8 | 8 | 8.76 | 1.62 | 8.0 |
| 8 | 10 | 7.89 | 1.79 | 10.0 |
| 8 | 12 | 7.12 | 1.98 | 12.0 |
| 8 | 16 | 6.14 | 1.97 | 8.4 |
| 10 | 6 | 9.73 | 1.48 | 6.0 |
| 10 | 8 | 8.76 | 1.62 | 8.0 |
| 10 | 10 | 7.89 | 1.79 | 10.0 |

TABLE 15-continued

Simulated steady-state PK parameters for IR
and QD dosage forms containing pregabalin

| $t_R$ hours | $t_{100}$ hours | $C_{MAX}$ μg/mL | $C_{MIN}$[1] μg/mL | $t_{MAX}$[2] hours |
|---|---|---|---|---|
| 10 | 12 | 7.12 | 1.98 | 12.0 |
| 10 | 16 | 6.34 | 2.45 | 8.4 |

[1]$C_{MIN}$ occurs just prior to the administration of the next dosage (i.e., at 12 and 24 hours post administration for BID and QD dosage forms, respectively).
[2]Time following administration of latest dosage.
[3]IR formulation containing 300 mg of pregabalin, dosed twice daily.
[4]QD formulation containing 600 mg of pregabalin.

TABLE 16

Amount of pregabalin released from
dosage form as a function of time (normalized)

| Time/$t_{100}$ | % w/w dissolved |
|---|---|
| 0.0 | 0 |
| 0.0658 | 21 |
| 0.132 | 32 |
| 0.263 | 47 |
| 0.526 | 68 |
| 0.789 | 85 |
| 1.0 | 100 |

The invention claimed is:

1. A pharmaceutical composition comprising an active pharmaceutical ingredient and excipients, the active pharmaceutical ingredient comprising pregabalin, or a pharmaceutically acceptable complex, salt, solvate or hydrate thereof, and the excipients comprising a matrix forming agent and a swelling agent, the matrix forming agent comprising polyvinyl acetate and polyvinylpyrrolidone, and the swelling agent comprising cross linked polyvinylpyrrolidone and polyethylene oxide, wherein the pharmaceutical composition is adapted for once-daily oral dosing; wherein the pregabalin comprises from about 5% to about 60% of the pharmaceutical composition by weight; the matrix forming agent comprises from about 5% to about 45% of the pharmaceutical composition by weight, and the swelling agent comprises from about 15% to about 70% of the pharmaceutical composition by weight.

2. The pharmaceutical composition according to claim 1, wherein the active pharmaceutical ingredient is released over a period of time of about 12 hours to about 20 hours.

3. The pharmaceutical composition according to claim 1, in which the active pharmaceutical ingredient exhibits an in vivo steady-state $C_{max}$ of about 9 μg/mL or less, or an in vivo steady-state $C_{min}$ of about 0.7 μg/mL or greater, or an in vivo steady-state $C_{max}$ of about 9 μg/mL or less and an in vivo steady-state $C_{min}$ of about 0.7 μg/mL or greater.

4. The pharmaceutical composition according to claim 1, wherein the pharmaceutical composition is bioequivalent to an immediate release formulation comprising pregabalin, lactose monohydrate, maize, starch, and talc.

5. The pharmaceutical composition according to claim 1 in which:
a) said matrix forming agent comprises about 20% to about 35% of the pharmaceutical composition by weight, and;
b) said swelling agent comprises about 20% to about 55% of the pharmaceutical composition by weight.

6. The formulation according to claim 1 in which the polyvinyl acetate is present in the quantity of about 60% to about 90% by weight based on the total weight of the polyvinyl acetate and polyvinylpyrrolidone.

7. The formulation according to claim 1 in which the polyvinyl acetate is present in the quantity of about 70% to about 90% by weight based on the total weight of the polyvinyl acetate and polyvinylpyrrolidone.

8. A method of treating a condition or disorder in a subject which is responsive to pregabalin, the method comprising administering to the subject a pharmaceutical composition as in claim 1, wherein the pharmaceutical composition is administered orally once daily.

9. The method according to claim 8, wherein the condition or disorder is selected from epilepsy, pain, diabetic peripheral neuropathy, postherpetic neuralgia, physiological conditions associated with psychomotor stimulants, inflammation, gastrointestinal damage, alcoholism, insomnia, fibromyalgia, anxiety, depression, mania, and bipolar disorder.

10. A pharmaceutical formulation suitable for once-a-day administration comprising:
a) pregabalin, or a pharmaceutically acceptable complex, salt, solvate or hydrate thereof, present in the quantity of from about 5% to about 60%, based on the total weight of the formulation;
b) a matrix of polyvinyl acetate and polyvinylpyrrolidone, in which the polyvinyl acetate is present in the quantity of about 70% to about 90% based on the total weight of the polyvinyl acetate and polyvinylpyrrolidine and the matrix is present in the quantity of about 20% to 35% by weight, based on the total weight of the formulation;
c) cross linked polyvinylpyrrolidone, present in the quantity of about 10% to about 35% by weight, based on the total weight of the formulation, and;
d) polyethylene oxide, present in the quantity of about 5% to about 35% by weight, based on the total weight of the formulation.

11. The formulation according to claim 10 in which the cross linked polyvinylpyrrolidone is present in the quantity of from about 20% to about 30% by weight, based on the total weight of the formulation.

12. The formulation according to claim 10 in which the polyethylene oxide is present in the quantity of from about 10% to about 25% based on the total weight of the formulation.

13. A method of treating a condition or disorder in a subject which is responsive to pregabalin, the method comprising administering to the subject the formulation according to claim 10 once daily.

14. The method according to claim 13, wherein the condition or disorder is selected from epilepsy, pain, diabetic peripheral neuropathy, postherpetic neuralgia, physiological conditions associated with psychomotor stimulants, inflammation, gastrointestinal damage, alcoholism, insomnia, fibromyalgia, anxiety, depression, mania, and bipolar disorder.

15. The method according to claim 13, in which the active pharmaceutical ingredient exhibits an in vivo steady-state $C_{max}$ of about 9 μg/mL or less.

16. The method according to claim 13, in which the active pharmaceutical ingredient exhibits an in vivo steady-state $C_{min}$ of about 0.7 μg/mL or greater.

17. The method according to claim 13, in which the active pharmaceutical ingredient exhibits an in vivo steady-state $C_{max}$ of about 9 μg/mL or less and an in vivo steady-state $C_{min}$ of about 0.7 μg/mL or greater.

* * * * *